(12) United States Patent
Grisenti et al.

(10) Patent No.: US 10,144,756 B2
(45) Date of Patent: Dec. 4, 2018

(54) STABLE SOLID FORMS OF REGADENOSON

(71) Applicant: Euticals S.p.A., Milan (IT)

(72) Inventors: Paride Grisenti, Milan (IT); Elahi Shahrzad Reza, Milan (IT); Giuseppe Guazzi, Milan (IT); Maria Argese, Milan (IT)

( * ) Notice: Subject to any disclaimer, the term of this patent is extended or adjusted under 35 U.S.C. 154(b) by 220 days.

(21) Appl. No.: 14/876,993

(22) Filed: Oct. 7, 2015

(65) Prior Publication Data

US 2016/0024137 A1 Jan. 28, 2016

Related U.S. Application Data

(63) Continuation of application No. PCT/EP2014/057247, filed on Apr. 10, 2014.

(30) Foreign Application Priority Data

Apr. 11, 2013 (EP) ..................... 13163400

(51) Int. Cl.
*C07H 19/16* (2006.01)
*C07H 19/167* (2006.01)

(52) U.S. Cl.
CPC ........... *C07H 19/16* (2013.01); *C07H 19/167* (2013.01); *C07B 2200/13* (2013.01)

(58) Field of Classification Search
CPC .... C07H 19/167; C07H 19/16; C07B 2200/13
USPC ....................................... 536/27.4
See application file for complete search history.

(56) References Cited

U.S. PATENT DOCUMENTS 8,106,183 B2 * 1/2012 Zablocki ................ C07H 19/16
536/27.11

FOREIGN PATENT DOCUMENTS

| WO | 2008028140 | 3/2008 | |
|----|------------|--------|-----------|
| WO | WO 2008/028140 A1 * | 3/2008 | ............ A61K 31/52 |
| WO | 2012149196 | 11/2012 | |

OTHER PUBLICATIONS

International Search Report and Written Opinion issued in related application PCT/EP2014/057247 dated Aug. 2, 2014.

* cited by examiner

*Primary Examiner* — Ganapathy Krishnan
(74) *Attorney, Agent, or Firm* — Stradley Ronon Stevens & Young, LLP

(57) ABSTRACT

A process for the preparation of the amorphous form of Regadenoson of formula

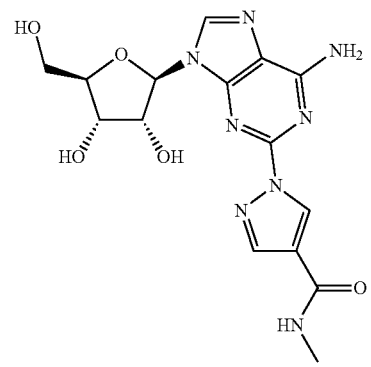

is disclosed together with new crystalline polymorphic forms E, F and G and methods for their preparation. Regadenoson amorphous form can be prepared in mild reaction conditions with high chemical purity (>99.6%) and high stability to the heating. A particularly thermodynamically stable anhydrous crystalline form of Regadenoson (form G) is also disclosed, provided with high stability not when exposed to 90% RH at 25° C. for 96 hour, but also to the heating up to 200° C.

23 Claims, 12 Drawing Sheets

STABLE SOLID FORMS OF REGADENOSON

CROSS REFERENCE TO RELATED APPLICATIONS

This application is a continuation of International Application No. PCT/EP2014/057247 filed Apr. 10, 2014, and claims priority to European Patent Application No. 13163400.8 filed Apr. 11, 2013, the entire contents of each application are incorporated by reference herein, in their entirety and for all purposes.

FIELD OF THE INVENTION

The present invention relates to the synthesis of organic compounds for use in pharmaceuticals as active agents. In particular, the present invention relates to a process for the preparation of stable solid forms of Regadenoson and the forms thereby obtained.

BACKGROUND OF THE INVENTION

The phenomenon of polymorphism is generated by the possibility that the same substance organizes in different crystalline forms (polymorphic forms), crystallizes with solvent molecules (hydrates and solvates) or solidifies without periodicity (amorphous substances).

The different crystalline or amorphous phases, even if of the same substance, can have different chemical, physical and mechanical properties and in case of active drug substances different characteristics of bioavailability and therapeutic efficiency. Furthermore, the same product in different crystalline or amorphous phases may present different characteristics of chemical stability.

Regadenoson (compound identified by Registry Number: 313348-27-5) was described for the first time in WO00/078779 and has the following structural formula

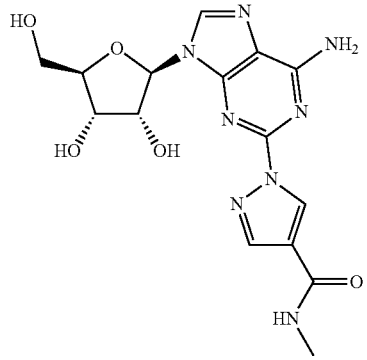 [SMILES: CNC(=O)c1cnn(-c2nc(N)c3ncn([C@@H]4O[C@H](CO)[C@@H](O)[C@H]4O)c3n2)c1]

This compound is an $A_{2A}$ adenosine receptor agonist responsible for regulating myocardial blood flow by vasodilating the coronary arteries and increasing blood flow to the myocardium. Regadenoson is employed as heart imaging aids where, prior to administration of an imaging agent, coronary arteries are dilated and then, by observation of the images thus produced, the diagnosis of a possible coronary artery disease (CAD) can be performed.

This compound is described to have different polymorphic forms identified as polymorphic forms A, B, C and D as well as an amorphous form.

The stability of these solid states is critical in order to allow the synthesis of this compound on a preparative scale. It is known by literature data that polymorphic form A, disclosed in U.S. Pat. No. 8,106,183, and D, disclosed in WO2012149196 are the more stable polymorphic forms and are the preferred solid states in which Regadenoson can be isolated and used for formulative purposes.

More in detail, polymorphic forms A, B, C and an amorphous form were disclosed in U.S. Pat. No. 8,106,183. In this patent, the crystalline forms are defined by means of X-Ray diffraction spectroscopy (XRD spectroscopy), differential scanning calorimetry data (DSC); the methods of preparation were also given.

Regadenoson polymorphic form A was identified as a monohydrate form; this form may be produced by crystallization of Regadenoson from protic solvents (for example ethanol or ethanol/water mixtures) or from a polar solvent (for example dimethylsulfoxide/water). Regadenoson Form A was identified by the authors of U.S. Pat. No. 8,106,183 as more stable than polymorphs B and C at ambient temperature and also under relative humidity stress conditions up to its melting point (identified by DSC as 194.5° C.).

Polymorphic forms B, C and the amorphous form were described as solid states, which could not easily prepared and/or proving unstable. Form B is prepared by evaporating under vacuum a solution of Regadenoson in trifluoroethanol at ambient temperature. However, its constitution could not be determined by the inventors of U.S. Pat. No. 8,106,183 because of X-ray disordered broad peaks, the polymorph contained variable amounts of water and its reliable preparation could not be reproduced. Polymorph C was prepared by slurrying Regadenoson in acetonitrile at 60° C. for a long period of time. This polymorph showed a distinct X-ray spectrum, but showed to be a variable hydrate, unstable at high temperatures.

In U.S. Pat. No. 8,106,183 the method of preparation of an amorphous form of Regadenoson is described by heating polymorphic form A at 200° C.; this solid state, differently by polymorphic forms A-C, was not described by the authors by an X-ray diffraction spectrum in order to identify possible characteristic halo-peaks (broad peaks). This amorphous form was prepared according to U.S. Pat. No. 8,106,183 by heating the polymorphic form A over the melting point value of this substance (that for polymorphic form A is 194.5° C.). This method is not industrially applicable and leads to the formation of several side products. The present inventors have found that this thermal treatment causes a decrease of chromatographic purity of about 30% and a change in the color of the sample (Regadenoson polymorphic form A is a white substance but after a thermal treatment at 190-200° C. the color changes to brown). To the best of our knowledge, this is the only described method for the preparation of amorphous Regadenoson.

Form D is disclosed in WO2012149196 as stable under inert conditions. This form contains between 0.8 and 1.7% by weight of water hydration and is indicated as useful for the preparation of solutions for administration, such as parenteral solutions. Form D is prepared through a complete new synthesis of Regadenoson, also disclosed in this reference. Regadenoson HPLC fractions of purity >99% are combined and concentrated to a paste. The supernatant is decanted and the flask is heated in an oil bath at 150° C. under reduced pressure of 20 mmHg for 6 hours to give Form D.

These literature data indicate that only the polymorphic forms A and D were identified as stable compounds, however, some precautions must be taken for their storage conditions and handling.

There is a strong need in the pharmaceutical industry for the preparation of stable solid forms of Regadenoson in an industrially easy and convenient manner. There is also the need for an easy and convenient process to convert the amorphous form into more thermodynamically stable polymorphic forms.

Moreover, there is also a strong need to have available solid forms of Regadenoson which are stable also in normal atmospheric conditions, in particular in humid conditions, without the need to store them in controlled atmospheric or inert conditions, with evident advantages in terms of handling and costs.

The present invention overcomes the technical problem of stability of polymorphic forms of Regadenoson by providing a process for the preparation of Regadenoson amorphous form and its conversion into new stable solid forms.

SUMMARY OF THE INVENTION

We have surprisingly found that Regadenoson amorphous form can be prepared in mild reaction conditions with high chemical purity (>99.6%) and that, under protected atmosphere, is stable to the heating (i.e. 80° C.) up to 96 hours; moreover this solid state does not give origin to degradation products in dry conditions when stored at 80° C. up to 96 hour and also when exposed to moisture at 25° C./90% RH up to 96 hours. The method of preparation of this amorphous form does not require extreme reaction temperatures (i.e. 200° C. as described in U.S. Pat. No. 81,906,183) and can be used for industrial preparative purposes.

In another embodiment of the present invention, Regadenoson amorphous form can be used to prepare other two stable solvate polymorphic forms, herein named Regadenoson form E (solvate with 1 molecule of trifluoroethanol) and Regadenoson form F (solvate with 0.5 molecule of ethanol).

In a further embodiment, also a particularly thermodynamically stable anhydrous crystalline form of Regadenoson, herein named form G, can be prepared from amorphous Regadenoson by refluxing in anhydrous ethanol for 60-90 hours. Regadenoson form G is characterized by an endothermic peak of fusion of about 265° C. (determined by DSC) and by a characteristic XRD spectrum. Regadenoson form G can be also conveniently isolated by direct precipitation from an anhydrous reaction mixture containing ethanol and methylamine at long reaction times (up to 90 hours). Generally, form G is prepared by converting the amorphous Regadenoson into the more thermodynamically stable crystalline anhydrous form G.

As for amorphous Regadenoson, these three new polymorphic forms are stable in dry conditions up to 96 hours at 80° C. and do not give origin to degradation products. Moreover, in wet conditions (i.e. 25° C./90% RH) these new polymorphic forms do not give origin to degradation products. Finally we have surprisingly found that also the crystalline phase of Regadenoson polymorphic form G (anhydrous form) shows an unusual high stability if compared to polymorphic forms A-F and to the amorphous form: in fact polymorphic form G is not only stable when exposed to 90% RH at 25° C. for 96 hour, but also to the heating up to 200° C.

The synthetic pathway for the preparation of amorphous Regadenoson according to the present invention is reported in the synthetic scheme 1. In this reaction scheme, conversion of 2-Halo adenosine (Hal=Chlorine or Iodine) into compound 2 follows the same procedure described in WO00/78779, WO2007092372 and Niiya, Kazunori et al. (Journal of Medicinal Chemistry, 35(24), 4557-61; 1992).

The synthetic step from compound 2 to amorphous Regadenoson is one object of the present invention and was developed in order to have the precipitation of this solid amorphous form directly from the reaction mixture in mild conditions with high chemical purity.

Scheme 1. Synthetic pathway of Regadenoson

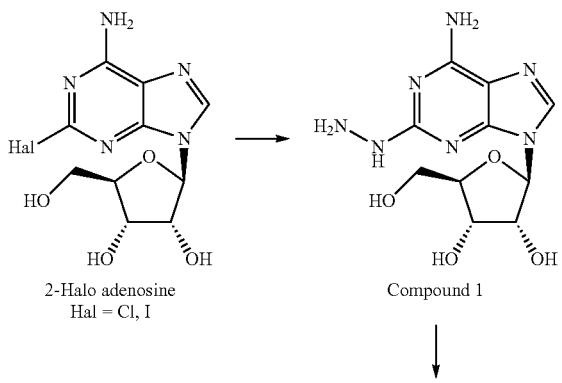

2-Halo adenosine
Hal = Cl, I

Compound 1

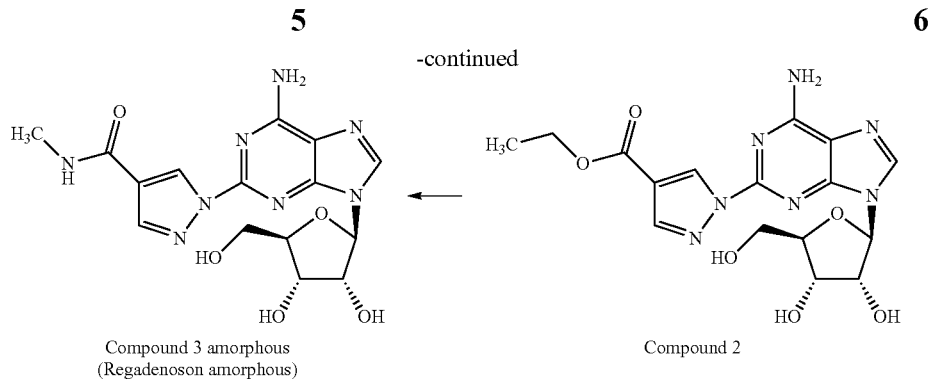

Compound 3 amorphous
(Regadenoson amorphous)

Compound 2

The present invention will be now disclosed in the foregoing description also by means of figures and examples.

DETAILED DESCRIPTION OF THE INVENTION

Figure 1:
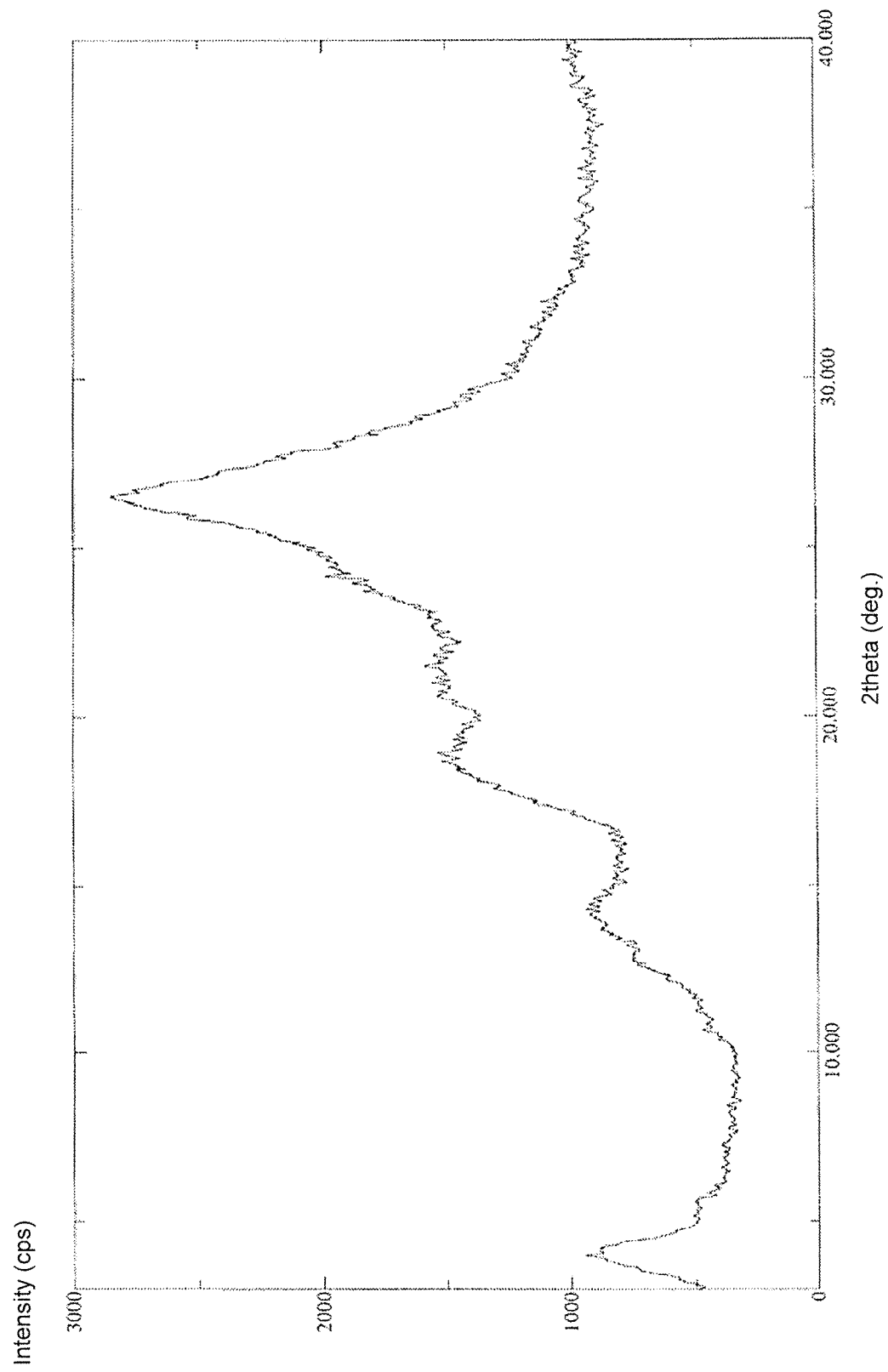
FIG. 1: XRD of Regadenoson amorphous form.

According to the present invention, and referring to the above Scheme 1, the process for the preparation of amorphous form of Regadenoson comprises the following steps:
a) reacting 2-(4-ethoxycarbonylpyrazol-1-yl)adenosine (compound 2) with a dry solution of methylamine in a linear or branched $C_1$-$C_4$ alcohol to provide a reaction mixture;
b) maintaining said reaction mixture under stirring at a temperature comprised between 60-100° C. in a pressure reactor in order to obtain the conversion of compound 2 into (1-{9-[(4S, 2R, 3R, 5R)-3,4-dihydroxy-5-(hydroxymethyl)oxolan-2-yl]-6-aminopurin-2yl}pyrazol-4-yl)-N-methylcarboxa-mide (Regadenoson, compound 3);
c) removing unreacted methylamine from said reaction mixture;
d) cooling said reaction mixture from step c) to 10-25° C. at a cooling rate of 1-2° C. min;
e) diluting said reaction mixture from step d) 1:1 with a dry $C_1$-$C_4$ alcohol to provide a precipitate of amorphous (1-{9-[(4S,2R,3R,5R)-3,4-dihydroxy-5-(hydroxymethyl)oxolan-2-yl]-6-aminopurin-2yl}pyrazol-4-yl)-N-methylcarboxamide;
f) filtering said amorphous precipitate of step e) to isolate, and if desired
g) drying said precipitate.

In the following description, 2-(4-ethoxycarbonylpyrazol-1-yl)adenosine is also named Ethyl 1-{9-[(4S,2R,3R,5R)-3,4-dihydroxy-5-(hydroxymethyl)oxolan-2-yl]-6-aminopurin-2-yl}pyrazole-4-carboxylate and corresponds to Compound 2 in the above Scheme 1.

In the following description, (1-{9-[(4S,2R,3R,5R)-3,4-dihydroxy-5-(hydroxymethyl)oxolan-2-yl]-6-aminopurin-2yl}pyrazol-4-yl)-N-methylcarboxamide is Regadenoson and corresponds to compound 3 in the above Scheme 1.

The reaction mixture of step a) is kept under stirring in a pressure reactor. The pressure is for example in the range of about 1-5 Bar.

Preferably, the reaction in step b) is run until complete conversion to Regadenoson. Reaction time may depend on reaction conditions, the solvent used, reactant concentration. Typically, the reaction is run for about 20-40 hours.

$C_1$-$C_4$ alcohol is methanol, ethanol, propanol isopropanol, n-butanol, sec-butanol, t-butanol. Ethanol is preferred, even more preferred is dry (absolute) ethanol.

The reaction temperature is selected according to reactant concentrations, the desired speed and other considerations according to the reaction environment and equipment. The conditions can be set by the person of ordinary skill in the art. For example, compound 2 is soluble even at room temperature at 0.1 M, while at 0.5 M dissolution occurs at 80° C. In any case, the reaction occurs also in suspension.

Removal of unreacted methylamine in step c) can be done with any ordinary means, for example by distillation under vacuum at about 30-60° C. or at normal pressure at about 40° C.

The alcohol used in step e) is preferably the same alcohol used in the previous steps.

Drying the final product is a typical operation, which does not require detailed explanation. For example, drying can be performed under vacuum at 50-80° C. for 48-96 hours, preferably in inert atmosphere.

According to a preferred embodiment of the present invention, the reaction is carried out using anhydrous ethanol and the concentration of methylamine in ethanol is comprised between 10 and 40% w/w, preferably 33%. The molar concentration of compound 2 in the reaction mixture is comprised between 0.5 and 0.1 M preferably 0.25 M. The preferred reaction temperature is comprised between 80-85° C. at an operative pressure of about 3 Bar for a reaction time of about 30 hours.

In a preferred embodiment of the present invention, the workup of the reaction (steps c)-g)) is carried out by removing methylamine by distillation under vacuum (about 15% of the volume of reaction was distilled) at 40° C., cooling the reaction mixture at 20-25° C., diluting the reaction mixture 1:1 with anhydrous ethanol, maintaining the reaction mixture under stirring for 30-60' at 20-25° C. and recovering the precipitate by filtration. Advantageously, this type of workup allows obtaining at the same time the amorphous form of Regadenoson with a high chemical purity. The wet product is dried under vacuum at 60° C. for 72 hours to afford amorphous Regadenoson.

Amorphous form can be identified by standard techniques, well known to the person of ordinary skill in the art.

Diagnostic peaks of XRD spectrum are with 6 Halos: P1 (4.040 2θ, 32%, width about 2.000 2θ), P2 (14.080 2θ, 33%, width about 3.300 2θ), P3 (18.400 2θ, 52%, width about 3.300 2θ), P4 (21.520 2θ, 57%, width about 2.666 2θ), P5 (24.220 2θ, 68%, width about 1.666 2θ), P6 (26.480 2θ, 100%, width about 4.998 2θ)

DSC shows a one main exothermic peak at 245.6° C. (onset 236.6° C.) followed by one endothermic peak at 280.4° C.

Another object of the present invention is polymorphic form F of Regadenoson (solvate form with 0.5 moles of ethanol per mole of Regadenoson) and can be prepared by a process comprising:
a) treating amorphous Regadenoson in anhydrous ethanol, preferably at a concentration of 3-8% w/w under inert atmosphere, to provide a suspension;
b) maintaining said suspension at a temperature comprised between 15-40° C. for 8-15 hours, to obtain a precipitate;
c) recovering said precipitate, for example by filtration; and if desired
d) drying said recovered precipitate under vacuum, for example at 40-80° C. for 48-96 hours.

According to a preferred embodiment, in step a) the relative ratio between amorphous Regadenoson and ethanol is 5% w/w, in step b) said suspension is maintained under stirring at 20-25° C. for 8-10 hours and in step d) said drying conditions are 60° C. for 72 hours.

Polymorphic Form F can be identified by standard techniques, well known to the person of ordinary skill in the art.

Diagnostic peaks of XRD spectrum are: 2θ values (relative intensity): 6.42 (40%), 10.38 (30%), 12.20 (29%), 12.80 (21%), 13.80 (36%), 16.24 (40%), 16.84 (24%), 19.28 (30%), 19.96 (23%), 20.20 (24%), 20.70 (42%), 22.00 (32%), 22.58 (19%), 23.38 (19%), 23.80 (31%), 25.04 (100%), 25.60 (48%), 26.28 (22%), 27.18 (73%), 28.48 (22%).

NMR spectrum is characterized by $CH_3CH_2OH$ signals adding to the signals of the well-known NMR of the amorphous form.

Also, elemental analysis provides a confirmation of the solvate form.

DSC shows one endothermic peak at 189° C. (onset 183° C.).

Another object of the present invention is polymorphic form E of Regadenoson (solvate form with 1 mole of trifluoroethanol for mole of Regadenoson) and can be prepared by a process comprising:
a) treating amorphous Regadenoson in dry trifluoroethanol, preferably at a concentration of 1-3%, at a temperature comprised between 15-50° C. for 0.5-1.0 hour to provide a reaction mixture;
b) filtering said reaction mixture, recovering a filtrate
c) concentrating said filtrate under vacuum, typically at 40-60° C., to provide a residue;
d) maintaining said residue, preferably at the same temperature of concentration, under vacuum, for example for 24-72 hours.

According to a preferred embodiment, the relative ratio between amorphous Regadenoson and trifluoroethanol is 1% w/w and the solution is maintained under stirring at 20-25° C. for 0.5 hour. The preferred temperature of evaporation is about 40° C. and this temperature is maintained for 48 hours.

Polymorphic Form E can be identified by standard techniques, well known to the person of ordinary skill in the art.

Diagnostic peaks of XRD spectrum are: 2θ values (relative intensity): 4.98 (100%), 12.08 (31%), 14.66 (52%), 17.60 (33%), 17.96 (31%), 19.20 (69%), 19.62 (93%), 20.24 (41%), 20.78 (34%), 21.08 (33%), 21.52 (36%), 23.18 (37%), 24.10 (42%), 24.24 (39%), 25.08 (38%), 25.52 (46%), 26.02 (85%), 26.64 (62%), 27.36 (54%), 27.66 (59%), 27.84 (64%), 28.74 (39%)

NMR spectrum is characterized by $CF_3CH_2OH$ signals adding to the signals of the well-known NMR of the amorphous form.

Also, elemental analysis provides a confirmation of the solvate form.

DSC shows a broad endothermic peak at 145°.

Polymorphic form G of Regadenoson (Regadenoson anhydrous) can be prepared by a process comprising the following steps:
a) treating amorphous Regadenoson in dry ethanol, preferably at a concentration of 4-7% w/v at a temperature comprised between 70-78° C. for a time sufficient to convert said amorphous Regadenoson into the more stable thermodynamically form G, typically for 60-90 hours, to provide a reaction mixture;
b) cooling said reaction mixture down to 20-25° C. to provide a precipitate;
c) isolating said precipitate, for example by filtration;
d) drying said isolated precipitate under vacuum at 40-60° C. for 24-72 hours.

According to a preferred embodiment, the relative ratio between amorphous Regadenoson and ethanol is 5% w/v and the reaction mixture maintained under stirring at 80° C. for 70 hours. The preferred drying conditions are 60° C. for 24 hours.

Polymorphic form G can also be prepared directly from the reaction mixture disclosed in step b) of the above described process from compound 2 to amorphous Regadenoson. Once Compound 2 is converted into Regadenoson, the reaction is continued for a time sufficient to convert it into the more thermodynamically stable crystalline form G. Typically, the reaction is continued for at least 30 hours.

According to this embodiment, polymorphic form G of Regadenoson (crystalline anhydrous Regadenoson) is prepared by a process comprising:
a) reacting 2-(4-ethoxycarbonylpyrazol-1-yl)adenosine (compound 2) with a dry solution of methylamine in a linear or branched $C_1$-$C_4$ alcohol to provide a reaction mixture;
b) maintaining said reaction mixture under stirring at a temperature comprised between 60-100° C. in a pressure reactor in order to obtain the conversion of compound 2 into (1-{9-[(4S, 2R, 3R, 5R)-3,4-dihydroxy-5-(hydroxymethyl)oxolan-2-yl]-6-aminopurin- 2yl}pyrazol-4-yl)-N-methylcarboxami-de (Regadenoson, compound 3);

c) continuing the reaction for a time sufficient to convert Regadenoson into the more thermodynamically stable crystalline form G;

d) removing unreacted methylamine from said reaction mixture;

e) cooling said reaction mixture from step d) to 10-25° C. at a cooling rate of 1-2° C. min;

f) diluting said reaction mixture from step e) 1:1 with a dry $C_1$-$C_4$ alcohol to provide a precipitate of crystalline anhydrous Regadenoson form G;

g) isolating said precipitate of step f), for example by filtration, and if desired h) drying said precipitate.

According to a preferred embodiment the reaction is carried out using anhydrous ethanol and the concentration of methylamine in ethanol is comprised between 10 and 40%, preferably 33%. The molar concentration of compound 2 in the reaction mixture is comprised between 0.5 and 0.1 preferably 0.25 M. The preferred reaction temperature is comprised between 80-85° C. at an operative pressure of about 3 Bar for a reaction time of about 70 hours. The workup of the reaction is realized by removing methylamine by distillation under vacuum (about 15% of the volume of reaction was distilled) at 40° C., cooling the reaction mixture at 20-25° C., diluting the reaction mixture 1:1 with anhydrous ethanol, maintaining the reaction mixture under stirring for 30' at 20-25° C. and recovering the precipitate by filtration. The wet product was dried under vacuum at 60° C. for 72 hours to afford Regadenoson polymorphic form G.

Polymorphic Form G can be identified by standard techniques, well known to the person of ordinary skill in the art.

Diagnostic peaks of XRD spectrum are: 2θ values (relative intensity): 8.24 (100%), 14.90 (23%), 17.70 (20%), 18.16 (21%), 19.84 (20%), 21.92 (30%), 26.16 (44%), 27.68 (34%), 30.44 (21%).

Also, elemental analysis provides a confirmation of the anhydrous form.

DSC shows a main endothermic peak at 264.6° C.

Polymorphic Form G shows the important advantage of a great thermal stability also in wet conditions.

In the above identification of Regadenoson solid forms, the values of the several spectra and analytical data should be taken considering the possible errors, precision and accuracy typical of the kind of analytical technique used.

All the solid forms of Regadenoson of the present invention are stable from a chemical point of view, i.e. are characterized by high purity, especially in view of their use as drugs. Moreover, the solid forms according to the present invention are thermodynamically stable and form G particularly stable in stressed wet conditions.

The advantages of the present invention are to provide a non-destructive method for the preparation of amorphous Regadenoson, going through a synthetic path involving mild reaction conditions.

The solid stable forms are also advantageous from a regulatory point of view, since stability of a crystalline form is a requirement for drug registration.

Also, from the industrial point of view, storage of this kind of forms is advantageous for their longer shelf-life.

Another object of the present invention are pharmaceutical compositions comprising Regadenoson in one of the polymorphic forms E, F or G, or mixtures thereof. Pharmaceutical compositions are well known in the art, as well as their methods of preparation. See for example "Remington's Pharmaceutical Sciences", last edition. Examples of pharmaceutical compositions are also provided in the above-mentioned references, see for example WO2012/149196. The pharmaceutical composition according to the present invention comprises a therapeutically effective dose of Regadenoson in a polymorphic form E, F or G, or mixtures thereof, in admixture with conventional excipients and vehicles. Typical therapeutic dosages can be found in the art, in particular for the drug Lexiscan®. Preferred compositions are injectable formulations, for example pre-filled syringes containing 0.4 mg/5 ml active ingredient.

Particularly preferred are pharmaceutical compositions in the form of injectable formulations.

The following examples further illustrate the invention.

EXPERIMENTAL SECTION $^1$H NMR analyses were performed at 500 MHz with a Bruker FT-NMR AVANCE™ DRX500 spectrometer. The infrared spectra (IR) were registered on a Perkin Elmer instrument (Mod FTIR Spectrum one) equipped with universal ATR sampling. DSC were registered on a Perkin Elmer instrument (Mod. DSC7) at a heating rate of 20° C./min from 50° C. to 310° C. X-Ray Diffraction spectra were registered by means of diffractometer (Rigaku-D-Max) from a start angle [½ 2θ] of 5.000 to 60.000. The diffraction diagrams were obtained employing a Cu anode (Kα=1.54060 Å and Kα=1.54439 Å).

The HPLC method utilized for the determination of the chromatographic purity of Regadenoson is here reported:

column Prontosil C-18-AQ (250×4.6 mm, 5 μm)
column temperature: 45° C.
flow rate 1.5 ml/min
detector UV=260 nm
gradient elution: time 0=95% phase A, 5% phase B; time 35'=75% phase A and 25% phase B; time 38'25% phase A and 75% phase B; time 40'=95% phase A and 5% phase B.
phase A composition: 97% water/0.1% triethylamine/0.1% acetic acid/3.0% acetonitrile (v/v/v/v)
phase B composition: 10% of Phase A and 90% of acetonitrile (v/v)

Example 1

Method A. Preparation of 2-Hydrazinoadenosine (Compound 1) from 2-Chloroadenosine A mixture of 2-Chloroadenosine (100 g; 0.33 moles) and hydrazine hydrate (60-65% in water; 300 ml) was stirred while heating to 40-45° C. for 2.5 hours. The reaction mixture was then brought to 20-25° C. and diluted under stirring with 96% ethanol (900 ml); the reaction mixture was then maintained under stirring for 8-10 hours and the precipitate collected by filtration. The filter cake was sequentially washed with water (400 ml) and ethanol cooled at 0° C. (400 ml); the solid recovered was dried under reduced pressure for 24 hours at 40° C. to afford 2-hydrazinoadenosine (80 g, 0.27 moles; 81% molar yield).

Method B. Preparation of 2-Hydrazinoadenosine (Compound 1) from 2-Iodoadenosine

A mixture of 2-Iodoadenosine (100 g; 0.25 moles), hydrazine monohydrate (98%; 80 ml) in 96% Ethanol (300 ml) was stirred at 40-45° C. for about 2 hours. The reaction mixture was then brought to 20-25° C. and diluted under stirring with 96% ethanol (300 ml); the reaction mixture was then maintained under stirring for 8-10 hours and the precipitate collected by filtration. The filter cake was washed with 96% ethanol (2×140 ml) cooled to 0° C.; the solid recovered was dried under reduced pressure for 24 hours at 40° C. to afford 2-hydrazinoadenosine (66 g, 0.22 moles; 88% molar yields).

Compound 1 obtained according to methods A and B showed the same chemical-physical properties:

$^1$H-NMR (DMSO-d6). δ 3.55 (m, 1H), 3.62 (m, 1H), 3.0-4.0 (2bs partially overlapped to the previous system; 3H), 3.80 (dd, 1H), 4.15 (dd, 1H), 4.60 (t, 1H), 5.10 (bs, 2H), 5.90 (d, 1H), 6.90 (br s, 2H), 7.25 (s, 1H), 7.98 (s, 1H).

MS (ESI positive): detectable the protonated molecular ion at m/z=298.4

IR (ATR). cm$^{-1}$: 3504, 3435, 3324, 3156, 2941, 2913, 1643, 1585, 1476, 1049, 1030.

Example 2

Ethyl 1-{9-[(4S,2R,3R,5R)-3,4-dihydroxy-5-(hydroxymethyl)oxolan-2-yl]-6-aminopurin-2-yl}pyrazole-4-car-boxylate which can Also be Identified as 2-(4-ethoxycarbonylpyrazol-1-yl)adenosine (Compound 2)

To a suspension of 2-hydrazinoadenosine (25 g, 80 mmol) in a 1:1 mixture of MeOH/AcOH (450 ml) was added (ethoxycarbonyl)malondialdehyde (19 g, 120 mmol) and the mixture was heated at 80° C. for 3 h. The precipitate formed was collected by filtration and washed with ethanol and diethyl ether to afford 30 g (74 mmol; 92% molar yields) of compound (2) as acetate salt.

$^1$H-NMR (DMSO-d6) δ 1.25 (t, 3H), 1.98 (s, 2.3H acetate), 3.58 (m, 1H), 3.68 (m, 1H), 3.90 (dd, 1H), 4.15 (dd, 1H), 4.25 (q, 2H), 4.60 (t, 1H), 5.0 (bs, 1H), 5.20 (bs, 1H), 5.50 (bs, 1H), 5.90 (d, 1H), 7.80 (br s, 2H), 8.08 (s, 1H), 8.4 (s, 1H), 8.9 (s, 1H).

IR (ATR). cm$^{-1}$: 3486, 3334, 3195, 2982, 2941, 1712, 1660, 1609, 1489, 1018, 982.

MP: 161.4° C.

MS (ESI positive): detectable the protonated molecular ion at m/z=406.5

Example 3

Amorphous (1-{9-[(4S,2R,3R,5R)-3,4-dihydroxy-5-(hydroxymethyl)oxolan-2-yl]-6-aminopurin-2yl}pyrazol-4-yl)-N-methylcarboxamide (Compound 3)

Compound 2 (21 g, 52 mmol) was suspended under stirring at 20-25° C. in 33% solution of methylamine in absolute ethanol (210 ml). The mixture was heated under stirring at 80-85° C. in a pressure reactor for 30 hours. After this period, the reaction mixture was concentrated under vacuum (12 mmHg) at 40° C. to about 85% of the initial volume (i.e. to a final reaction volume of about 178 ml). The reaction temperature was brought to 20-25° C., then diluted with absolute ethanol (200 ml). The mixture was maintained under stirring for 30' at 20-25° C. and the precipitate recovered by filtration, washed on the filter with absolute ethanol (200 ml) and dried under vacuum at 60° C. for 72 hours to afford 17 g (43.6 mmoles; 84% calculated on the dry substance) of compound 3 in an amorphous form with a chromatographic purity of 99.7% (determined by HPLC).

$^1$H-NMR (DMSO d6) δ 2.76 (d, 3H, 4.6 Hz; C$\underline{H_3}$—NH), 3.67 and 3.57 (m, 2H; C$\underline{H_2}$OH), 3.96 (m, 1H; C$\underline{H}$—CH$_2$), 4.17 (m, 1H; 3'C$\underline{H}$—OH), 4.62 (m, 1H; 2'C$\underline{H}$—OH), 5.02 (dd, 1H, 5.7 Hz; OH), 5.23 (bs, 1H; OH), 5.50 (d, 1H, 6.2 Hz; 2'OH), 5.94 (d, 1H, 6.2 Hz; O—CH—N), 7.77 (bs, 2H; NH$_2$), 8.07 (s, 1H; =N—N—C$\underline{H}$=), 8.35 (q, 1H; NH), 8.41 (s, 1H; N—CH=N), 8.95 (s, 1H; CH=N). These spectroscopic data are in agreement with the proposed structure and with literature data (U.S. Pat. No. 8,106,183).

XRD (FIG. 1). Amorphous Regadenoson with 6 Halos: P1 (4.040 2θ, 32%, width about 2.000 2θ), P2 (14.080 2θ, 33%, width about 3.300 2θ), P3 (18.400 2θ, 52%, width about 3.300 2θ), P4 (21.520 2θ, 57%, width about 2.666 2θ), P5 (24.220 2θ, 68%, width about 1.666 2θ), P6 (26.480 2θ, 100%, width about 4.998 2θ)

Figure 6:
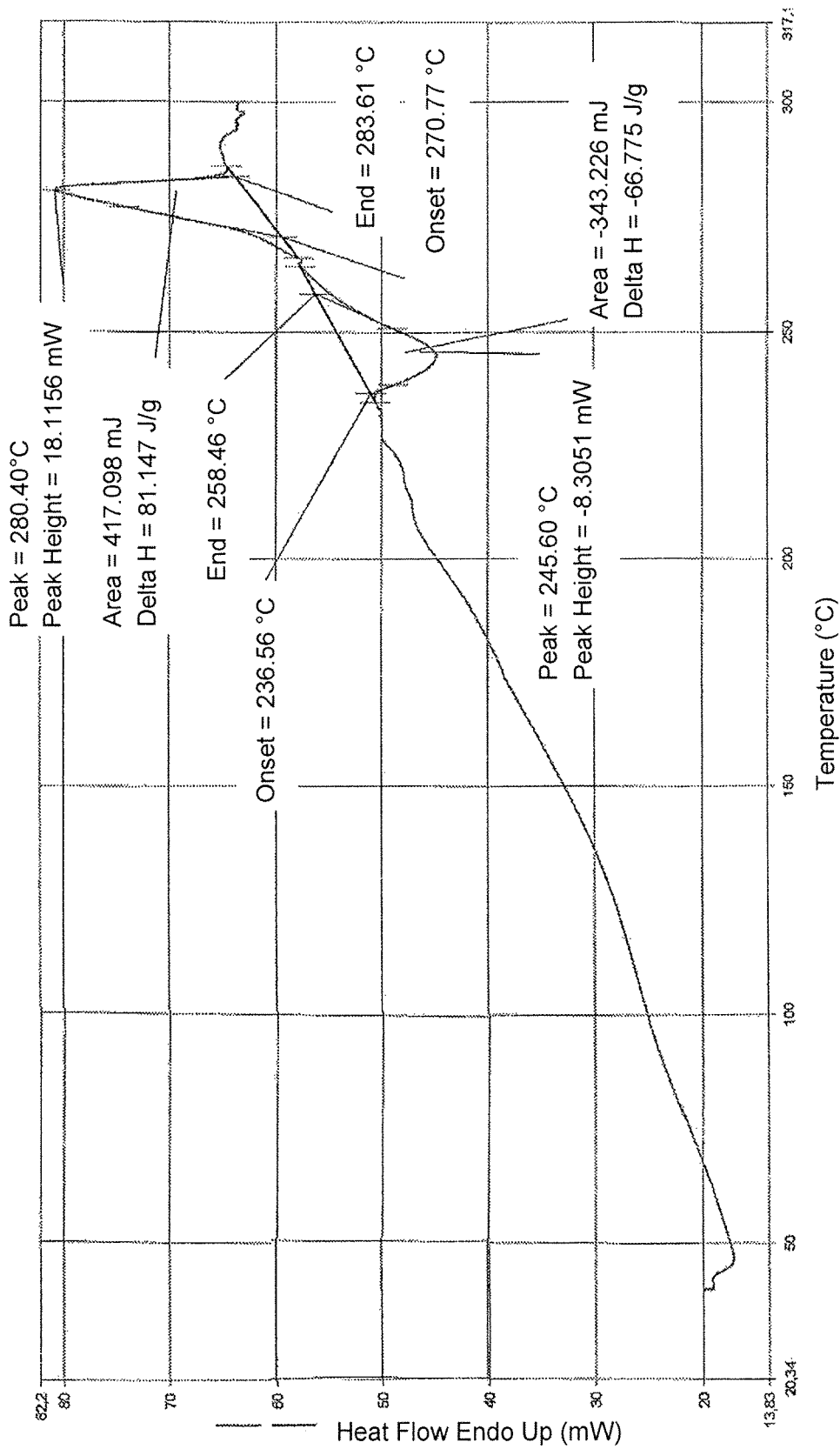
FIG. 6: Differential scanning calorimetry data of Regadenoson amorphous form.
Figure 7:
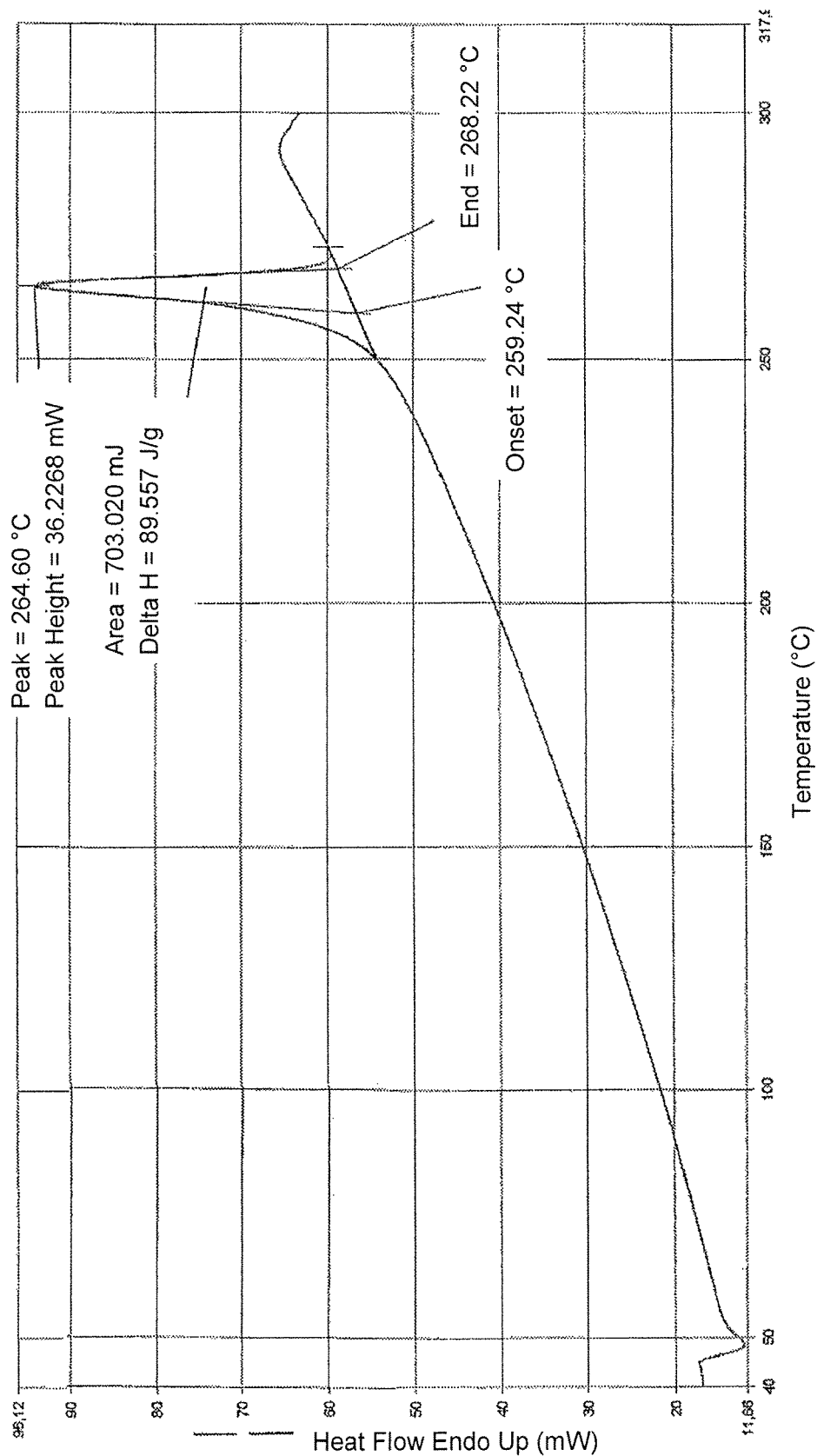
FIG. 7: Differential scanning calorimetry data of Regadenoson G (anhydrous form)
Figure 8:
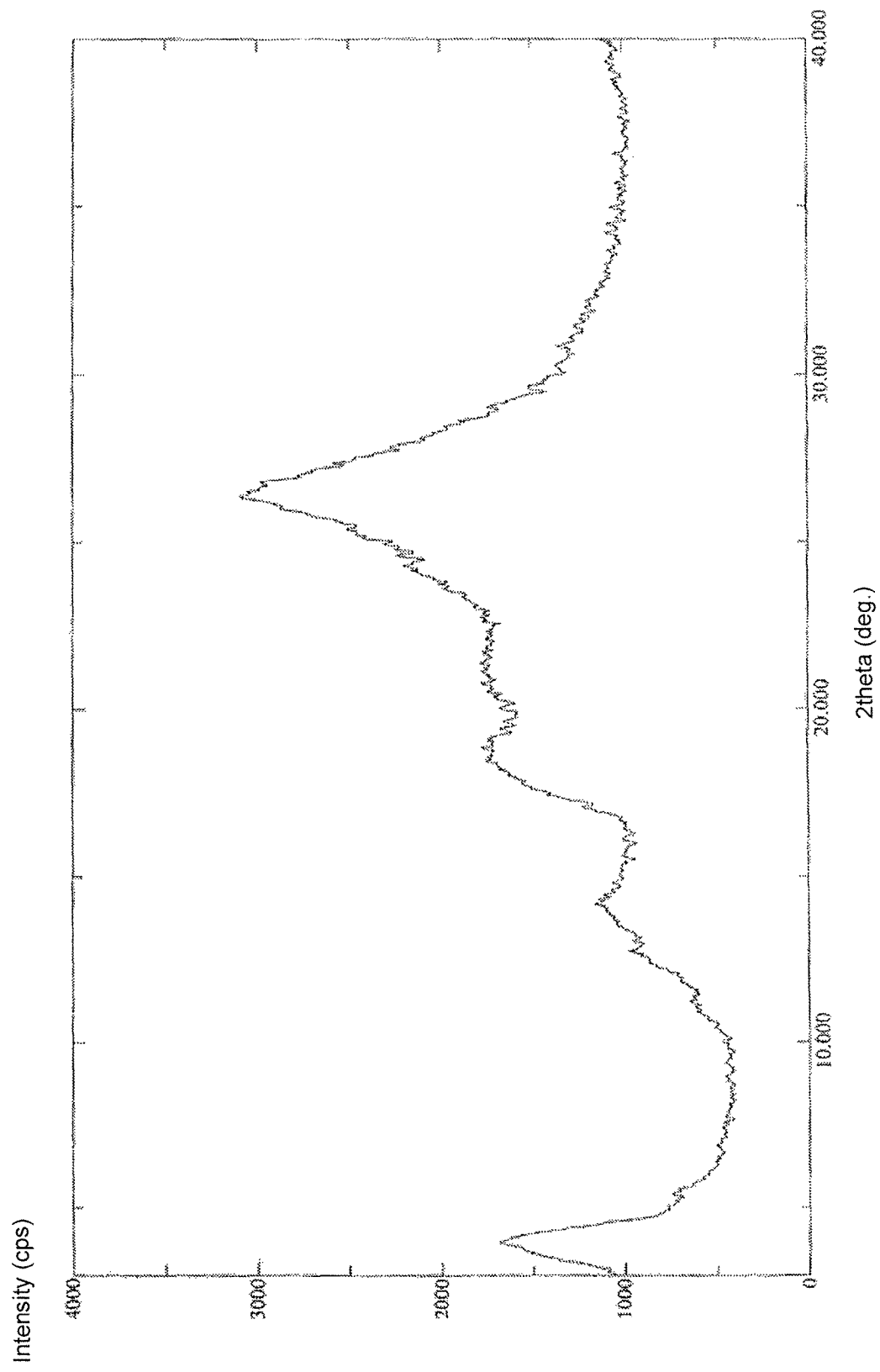
FIG. 8: Stability data of Regadenoson amorphous form: XRD after 96 hours at 80° C. under inert atmosphere.
Figure 9:
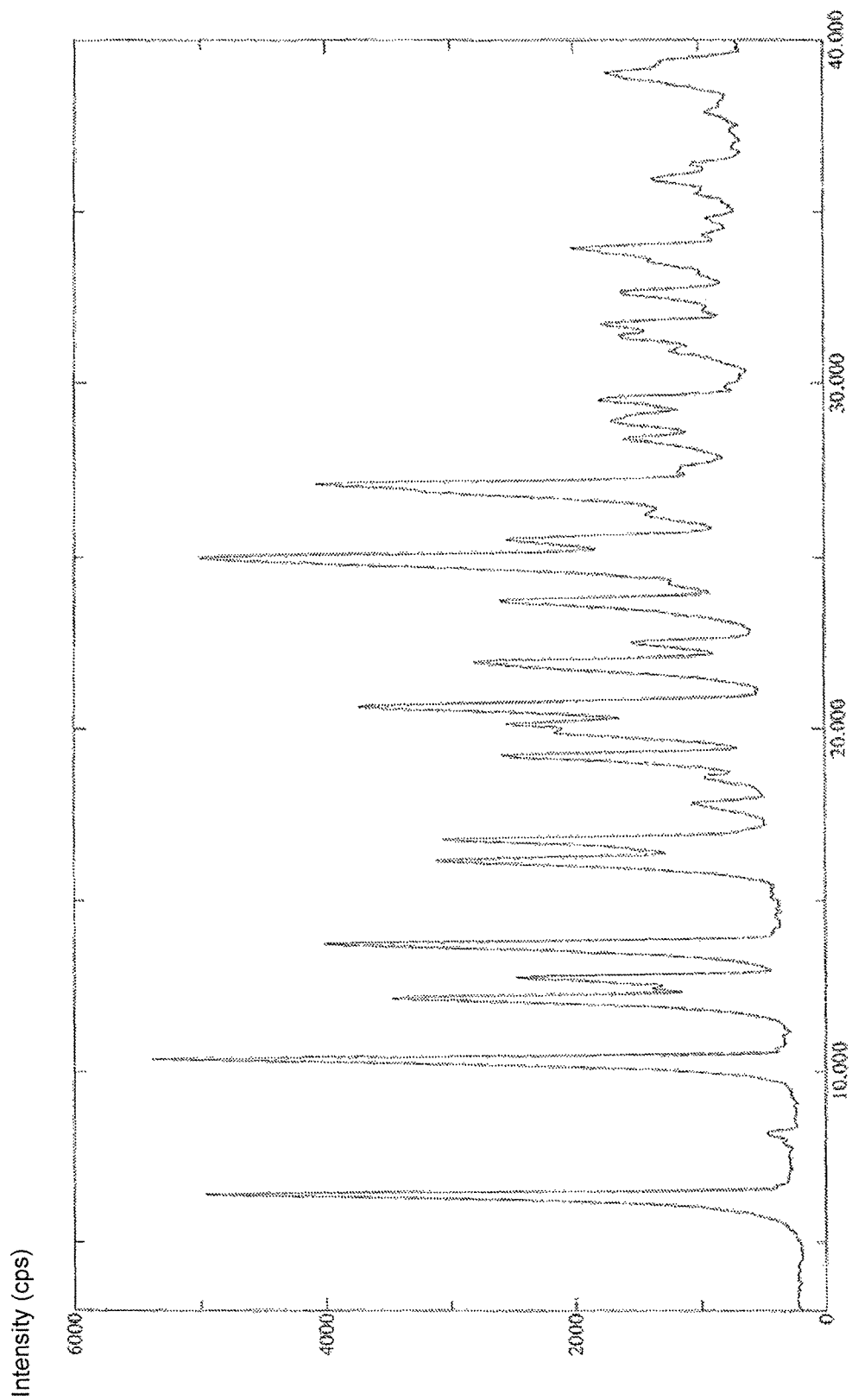
FIG. 9: Stability data of Regadenoson crystalline form F (solvate form with ethanol): XRD after 96 hours at 80° C. under inert atmosphere.
Figure 10:
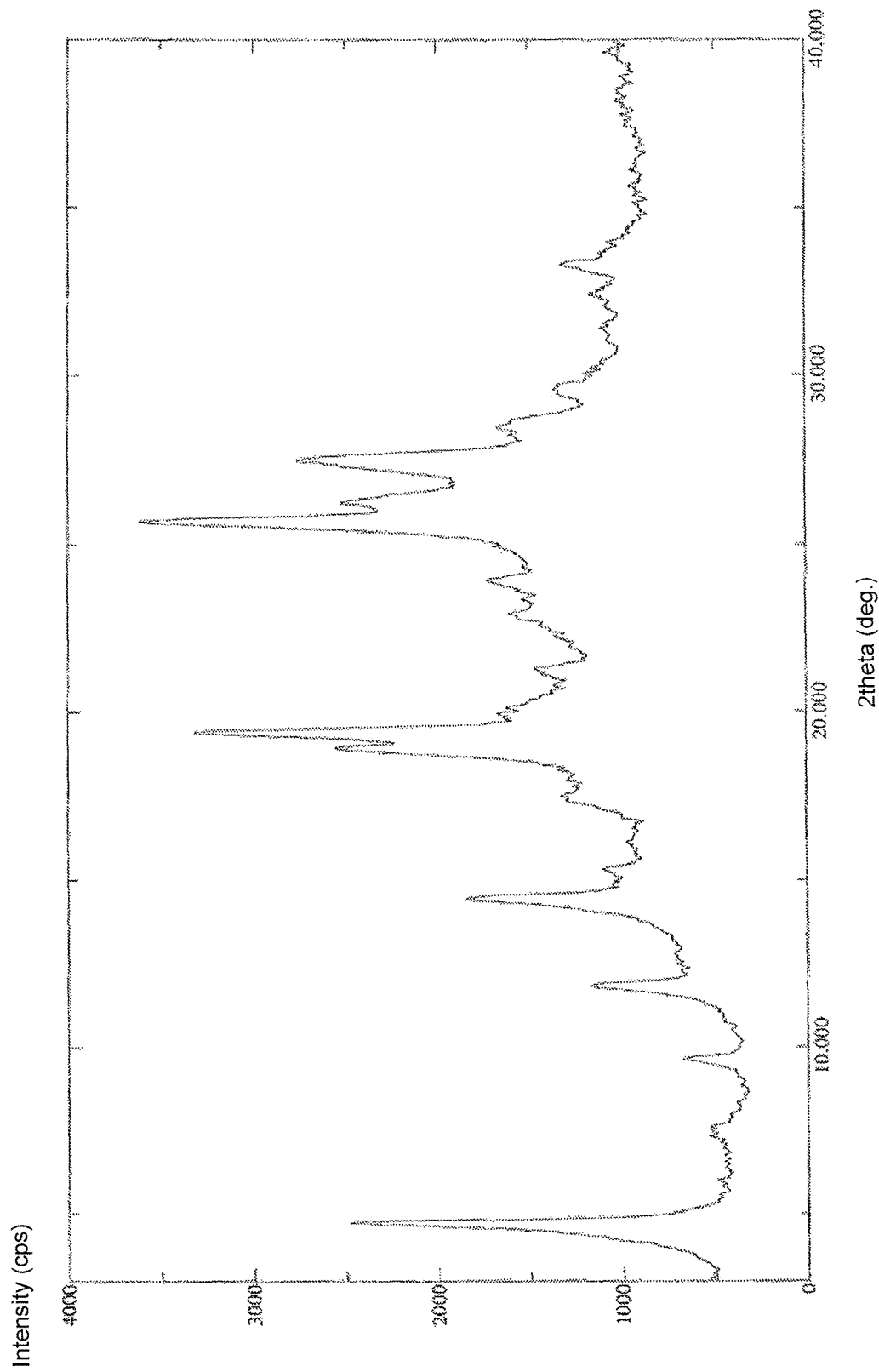
FIG. 10: Stability data of Regadenoson form E (solvate form with trifluoroethanol): XRD after 96 hours at 80° C. under inert atmosphere.
Figure 11:
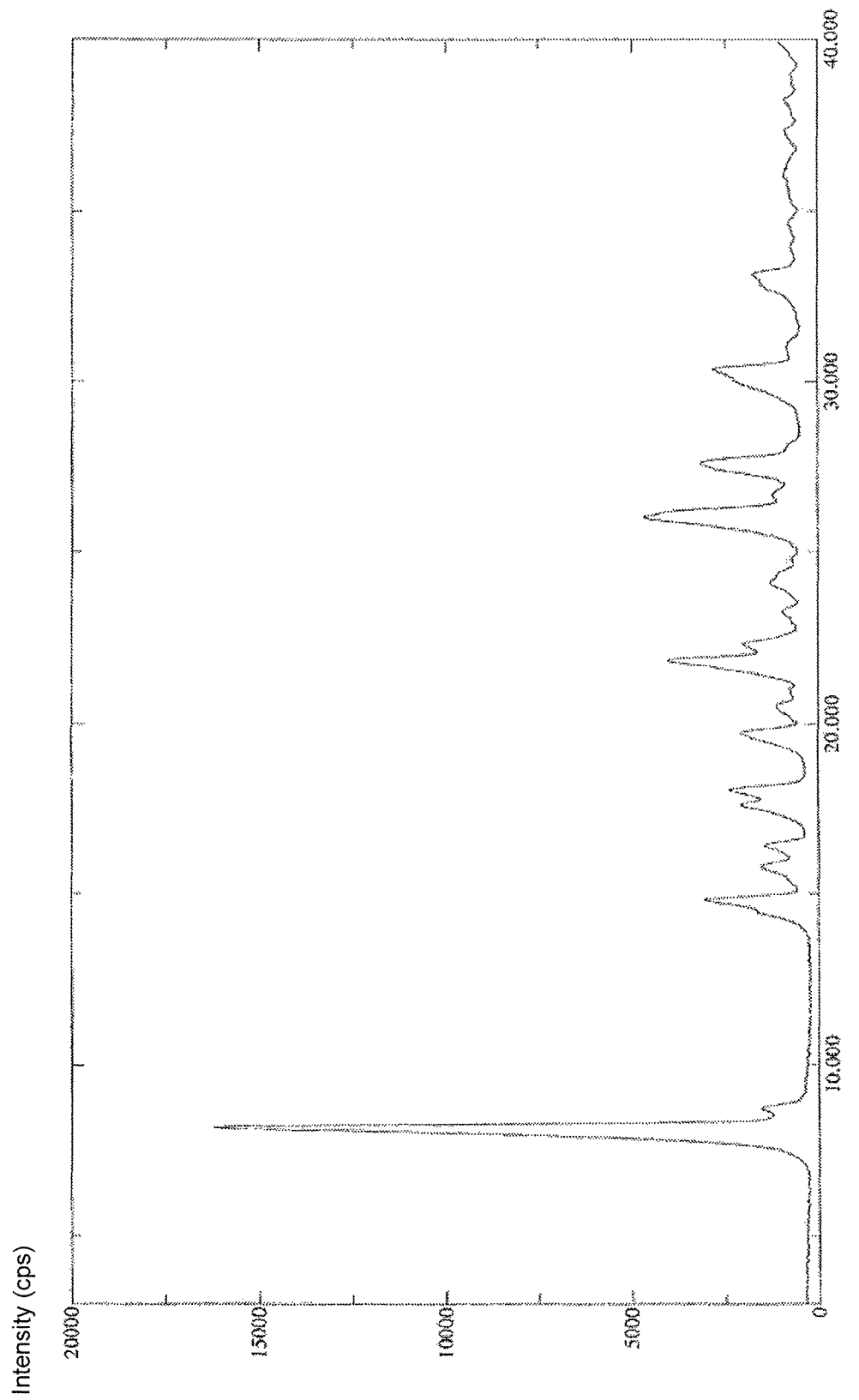
FIG. 11: Stability data of Regadenoson form G (anhydrous form): XRD after 96 hours at 80° C. under inert atmosphere.
Figure 12:
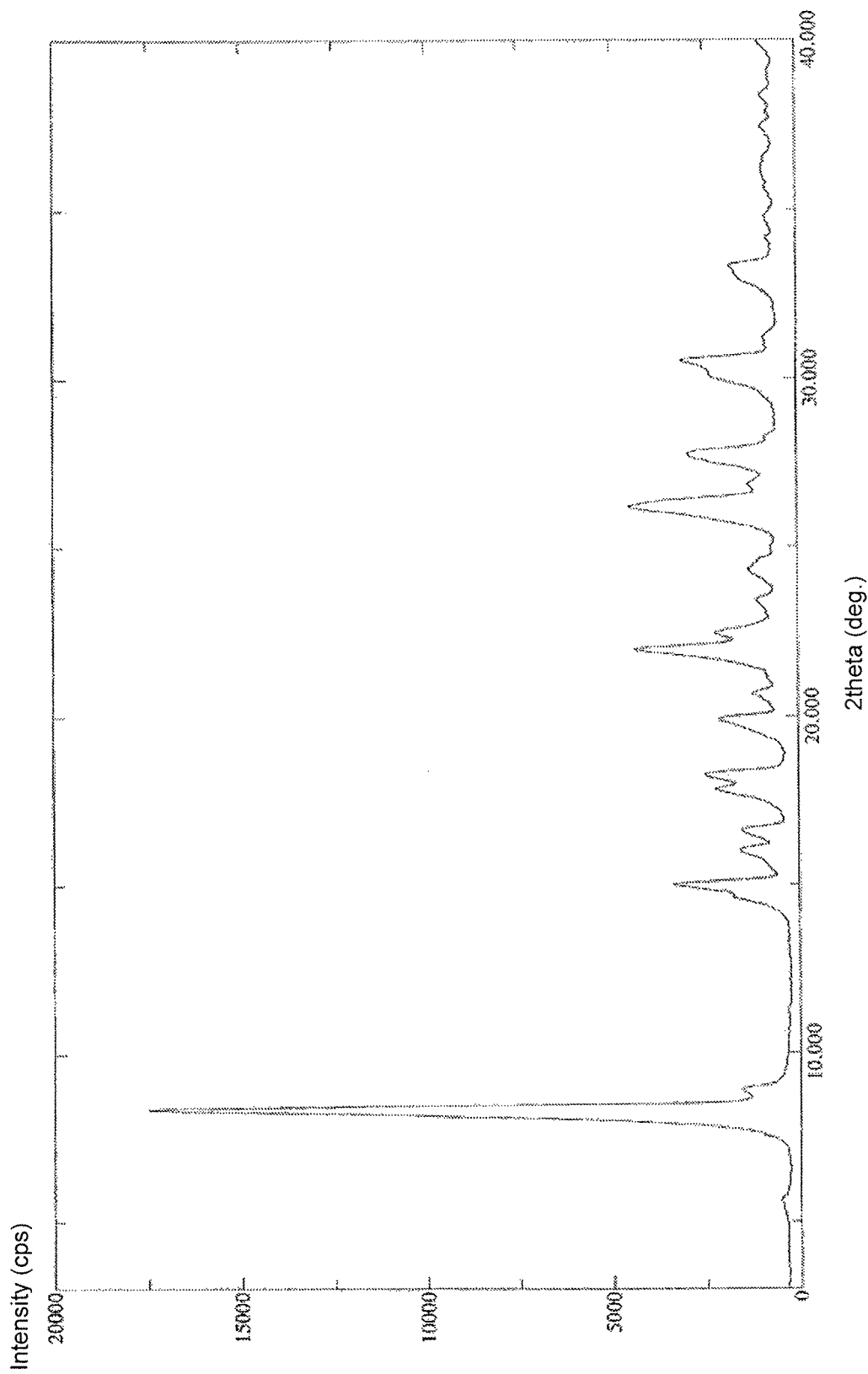
FIG. 12: Stability data of Regadenoson form G (anhydrous form): XRD after 96 hours at 25° C./90% RH.

DSC (FIG. 6). One main exothermic peak at 245.6° C. (onset 236.6° C.) followed by one endothermic peak at 280.4° C.

IR (ATR). cm$^{-1}$: 3317, 3216, 2933, 1640, 1604, 1574, 1404, 1340, 1284, 1130, 1087, 1059, 1019, 975, 912, 863, 724.

MS (ESI positive): detectable the protonated molecular ion at m/z=391.5

Example 4

Polymorphic Form F of (1-{9-[(4S,2R,3R,5R)-3,4-dihydroxy-5-(hydroxymethyl)oxolan-2-yl]-6-aminopurin-2yl}pyrazol-4-yl)-N-methylcarboxamide (Compound 3 Hemiethanolate)

Amorphous compound 3 (17 g) obtained from Example 3 was slurried in absolute ethanol (340 ml) under stirring at 20-25° C. and nitrogen atmosphere for 8-10 hours. After this period the solid was recovered by filtration, washed on the filter with absolute ethanol (250 ml) and dried under vacuum at 60° C. for 72 hours to afford 13 g of compound 3 in the polymorphic form F (67% molar yields). The HPLC purity of this compound is 99.7%

$^1$H-NMR (DMSO d6) δ 1.07 (t, 0.85H, C$\underline{H_3}$CH$_2$OH), 2.76 (d, 3H, 4.6 Hz; C$\underline{H_3}$—NH), 3.45 (dd, 0.57H, CH$_3$C$\underline{H_2}$OH) 3.67 and 3.57 (m, 2H; C$\underline{H_2}$OH), 3.96 (m, 1H; C$\underline{H}$—CH$_2$), 4.17 (m, 1H; 3'C$\underline{H}$—OH), 4.45 (t, 0.44H, CH$_3$CH$_2$O$\underline{H}$), 4.62 (m, 1H; 2'C$\underline{H}$—OH), 5.02 (dd, 1H, 5.7 Hz; OH), 5.23 (bs, 1H; OH), 5.50 (d, 1H, 6.2 Hz; 2'OH), 5.94 (d, 1H, 6.2 Hz; O—CH—N), 7.77 (bs, 2H; NH$_2$), 8.07 (s, 1H; =N—N—C$\underline{H}$=), 8.35 (q, 1H; NH), 8.41 (s, 1H; N—CH=N), 8.95 (s, 1H; CH=N).

Figure 2:
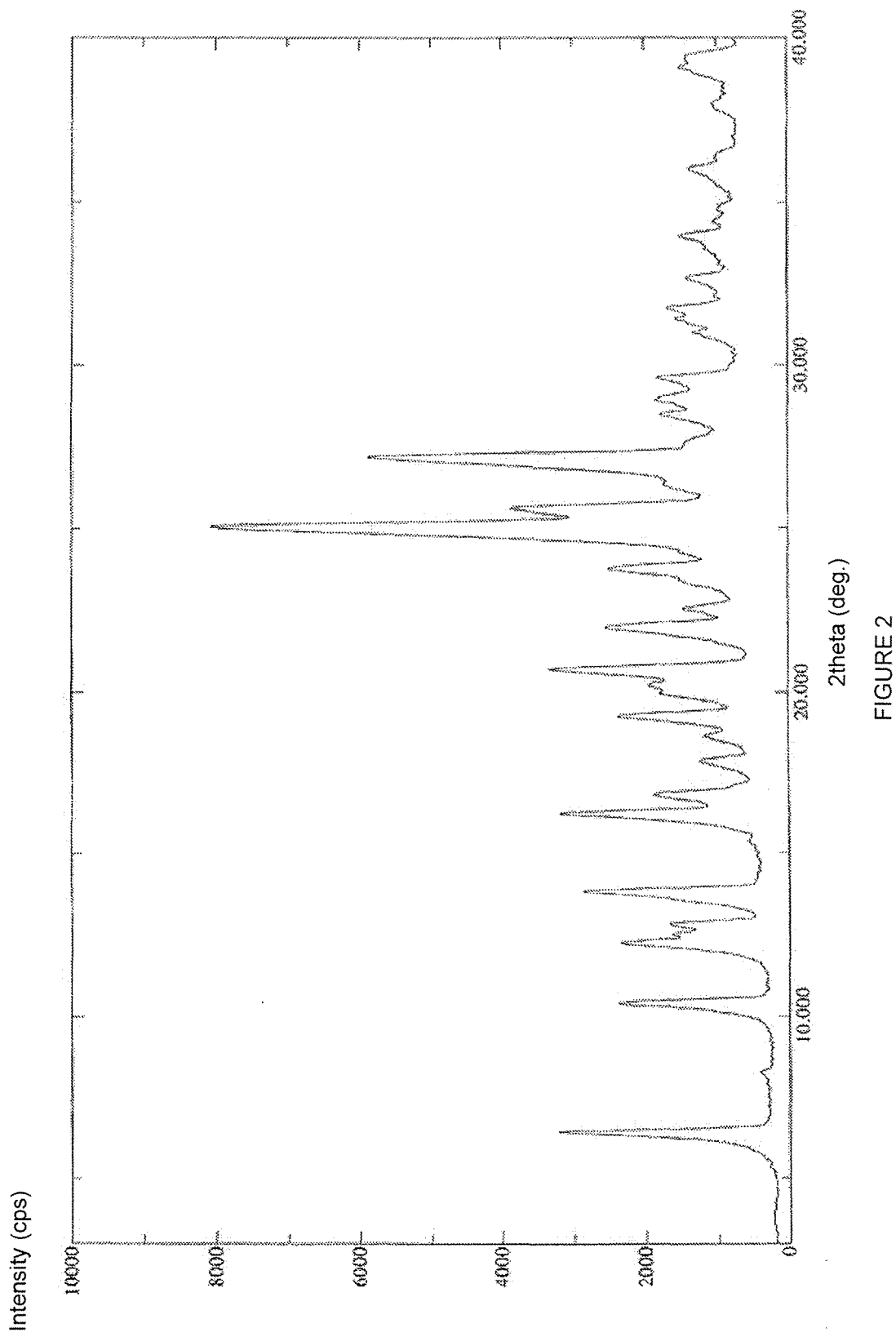
FIG. 2: XRD of Regadenoson crystalline form F (solvate form with ethanol)

XRD (FIG. 2). 2θ values (relative intensity): 6.42 (40%), 10.38 (30%), 12.20 (29%), 12.80 (21%), 13.80 (36%), 16.24 (40%), 16.84 (24%), 19.28 (30%), 19.96 (23%), 20.20 (24%), 20.70 (42%), 22.00 (32%), 22.58 (19%), 23.38 (19%), 23.80 (31%), 25.04 (100%), 25.60 (48%), 26.28 (22%), 27.18 (73%), 28.48 (22%)

DSC: main endothermic peak at 189° C.

IR (ATR). cm$^{-1}$: 3498, 3348, 3309, 3127, 3081, 2972, 2938, 1639, 1620, 1583, 1485, 1450, 1407, 1335, 1287, 1279, 1211, 1132, 1121, 1050, 1036, 1012, 980, 969, 919, 903, 886, 809, 790, 722, 665.

Elemental analysis data calculated for C$_{15}$H$_{18}$N$_8$O$_5$. ½ C$_2$H$_6$O$_1$. Theoretical values: C=46.49%, H=5.12%, O=21.29%, N=27.11%. Found: C=46.55%, H=5.15%, O=21.35%, N=26.95%.

Example 5

Polymorphic Form E of (1-{9-[(4S,2R,3R,5R)-3,4-dihydroxy-5-(hydroxymethyl(oxolan-2-yl]-6-aminopurin-2yl}pyrazol-4-yl)-N-methylcarboxamide (Compound 3 Trifluoroethanolate)

1 g (2.56 mmoles) amorphous compound 3 obtained according to Example 3 were dissolved in 2,2,2-trifluoroethanol (100 ml) under stirring at 20-25° C. and nitrogen atmosphere and maintained under stirring for 30'. After this period, the solution was filtered (0.45 μm cutoff); the filtrate concentrated under vacuum at 40° C. to residue to afford compound 3 in the polymorphic form E (980 mg).

$^1$H-NMR (DMSO d6) δ 2.78 (d, 3H, 4.6 Hz; CH$_3$—NH), 3.67 and 3.57 (m, 2H; CH$_2$OH), 3.93 (dd, CF$_3$CH$_2$OH). 3.98 (m, 1H; CH—CH$_2$), 4.19 (bs, 1H; 3'CH—OH), 4.62 (d, 1H; 2'CH—OH), 5.02 (dd, 1H, 5.7 Hz; OH), 5.23 (bs, 1H; OH), 5.50 (d, 1H, 6.2 Hz; 2'OH), 5.94 (d, 1H, 6.2 Hz; O—CH—N), 6.08 (bs, CF$_3$CH$_2$OH), 7.77 (bs, 2H; NH$_2$), 8.07 (s, 1H; =N—N—CH=), 8.35 (q, 1H; NH), 8.41 (s, 1H; N—CH=N), 8.95 (s, 1H; CH=N).

Figure 3:
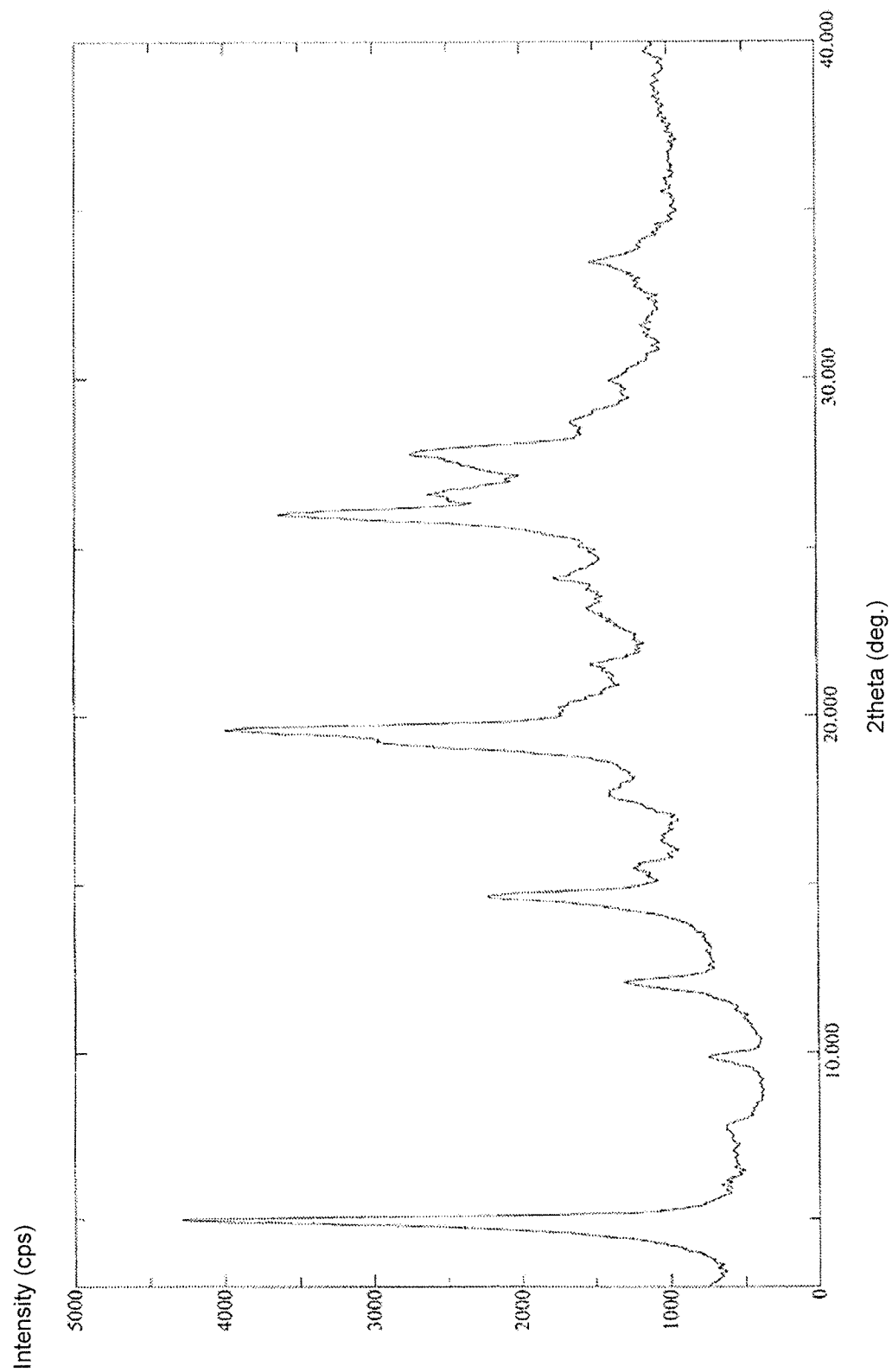
FIG. 3: XRD of Regadenoson form E (solvate form with trifluoroethanol)

XRD (FIG. 3). 2θ values (relative intensity): 4.98 (100%), 12.08 (31%), 14.66 (52%), 17.60 (33%), 17.96 (31%), 19.20 (69%), 19.62 (93%), 20.24 (41%), 20.78 (34%), 21.08 (33%), 21.52 (36%), 23.18 (37%), 24.10 (42%), 24.24 (39%), 25.08 (38%), 25.52 (46%), 26.02 (85%), 26.64 (62%), 27.36 (54%), 27.66 (59%), 27.84 (64%), 28.74 (39%)

DSC: broad endothermic peak at 145° C.

IR (ATR). cm$^{-1}$: 3341, 3270, 3127, 2920, 1643, 1578, 1537, 1519, 1488, 1449, 1423, 1413, 1369, 1342, 1276, 1197, 1141, 1090, 1060, 1023, 980, 947, 901, 852, 826, 807, 788.

Elemental analysis data calculated for $C_{15}H_{18}N_8O_5 \cdot C_2H_3O_1F_3$. Theoretical values: C=41.64%, H=4.32%, O=19.57%, N=22.85%, F=11.62%. Found: C=41.84%, H=4.52%, O=19.56%, N=22.65%, F=11.42%.

Example 6

Polymorphic Form G of (1-{9-[(4S,2R,3R,5R)-3,4-dihydroxy-5-(hydroxymethyl)oxolan-2-yl]-6-amin-opurin-2yl}pyrazol-4-yl)-N-methylcarboxamide (Compound 3 Anhydrous) from Amorphous Compound 3

Amorphous compound 3 (500 mg; 1.28 mmoles) obtained from Example 3 was slurried in absolute ethanol (10 ml) under stirring at 80° C. and nitrogen atmosphere for 70 hours. After this period the reaction mixture was brought to 20-25° C. and the solid was recovered by filtration, washed on the filter with absolute ethanol (5 ml) and dried under vacuum at 60° C. for 24 hours to afford 450 mg of compound 3 in the polymorphic form G (90% molar yields). The HPLC purity of this compound is 99.8%

$^1$H-NMR (DMSO d6) δ 2.76 (d, 3H, 4.6 Hz; CH$_3$—NH), 3.66 and 3.56 (m, 2H; CH$_2$OH), 3.96 (m, 1H; CH—CH$_2$), 4.18 (m, 1H; 3'CH—OH), 4.62 (m, 1H; 2'CH—OH), 5.04 (dd, 1H, 5.7 Hz; OH), 5.26 (bs, 1H; OH), 5.52 (d, 1H, 6.2 Hz; 2'OH), 5.94 (d, 1H, 6.2 Hz; O—CH—N), 7.78 (bs, 2H; NH$_2$), 8.07 (s, 1H; =N—N—CH=), 8.36 (q, 1H; NH), 8.42 (s, 1H; N—CH=N), 8.96 (s, 1H; CH=N).

Figure 4:
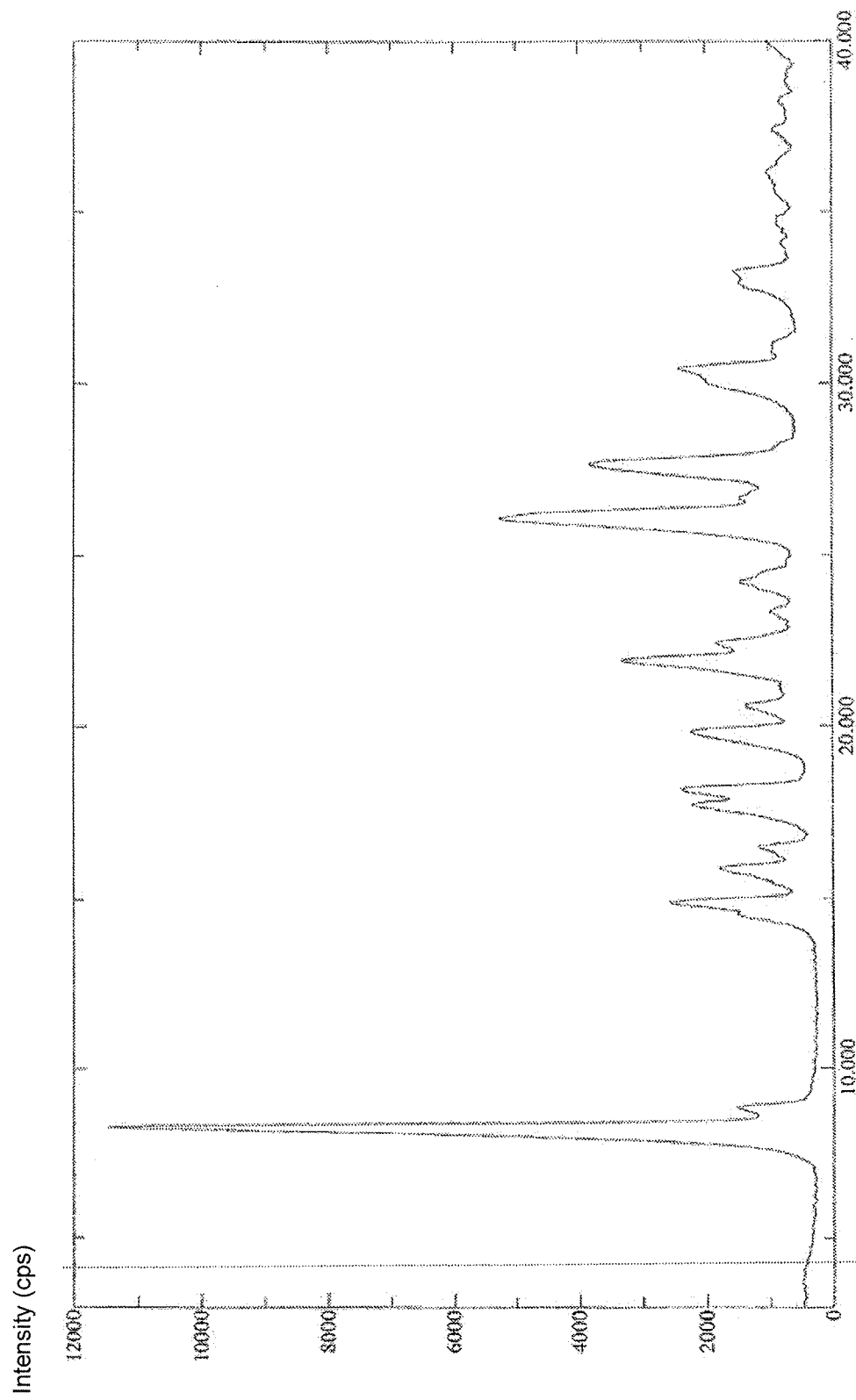
FIG. 4: XRD of Regadenoson form G (anhydrous form)

XRD (FIG. 4) 2θ values (relative intensity): 8.24 (100%), 14.90 (23%), 17.70 (20%), 18.16 (21%), 19.84 (20%), 21.92 (30%), 26.16 (44%), 27.68 (34%), 30.44 (21%)

DSC: main endothermic peak at 264.6° C.

IR (ATR). cm$^{-1}$: 3329, 3292, 3225, 3159, 3142, 3100, 3021, 2926, 2893, 1665, 1635, 1595, 1559, 1487, 1439, 1417, 1394, 1357, 1340, 1322, 1234, 1214, 1197, 1126, 1075, 1054, 1045, 1032, 1012, 992, 976, 919, 859, 850, 817, 790, 744, 715, 671.

Elemental analysis data calculated for $C_{15}H_{18}N_8O_5$. Theoretical values: C=46.15%, H=4.65%, O=20.49%, N=28.71%. Found: C=46.11%, H=4.67%, 0=20.52%, N=28.75%.

Example 7

Polymorphic Form G of (1-{9-[(4S,2R,3R,5R)-3,4-dihydroxy-5-(hydroxymethyl)oxolan-2-yl]-6-amin-opurin-2yl}pyrazol-4-yl)-N-methylcarboxamide (Compound 3 Anhydrous) Form Compound 2

Compound 2 (25.2 g, 62.4 mmoles) was suspended under stirring at 20-25° C. in 33% solution of methylamine in absolute ethanol (252 ml). The mixture was heated under stirring at 80-85° C. in a pressure reactor for 70 hours (the pressure registered on the reaction vessel was of 3 Bar). After this period, the reaction mixture was concentrated under vacuum (12 mmHg) at 40° C. to about 85% of the initial volume (i.e. to a final reaction volume of about 214 ml). The reaction temperature was brought to 20-25° C. then diluted with absolute ethanol (240 ml). The mixture was maintained under stirring for 30' at 20-25° C. and the precipitate recovered by filtration, washed on the filter with absolute ethanol (240 ml) and dried under vacuum at 60° C. for 72 hours to afford 19.7 g (50.5 mmoles; 80%) of compound 3 in an anhydrous form with a chromatographic purity of 99.8% (determined by HPLC).

The chemical-physical properties of the obtained compound 3 are the same obtained from Example 6.

Example 8

Preparation of Polymorphic Form A of (1-{9-[(4S,2R,3R,5R)-3,4-dihydroxy-5-(hydroxymethyl)oxo-lan-2-yl]-6-aminopurin-2yl}pyrazol-4-yl)-N-methyl-carboxamide (Compound 3) According to U.S. Pat. No. 8,106,183

Figure 5:
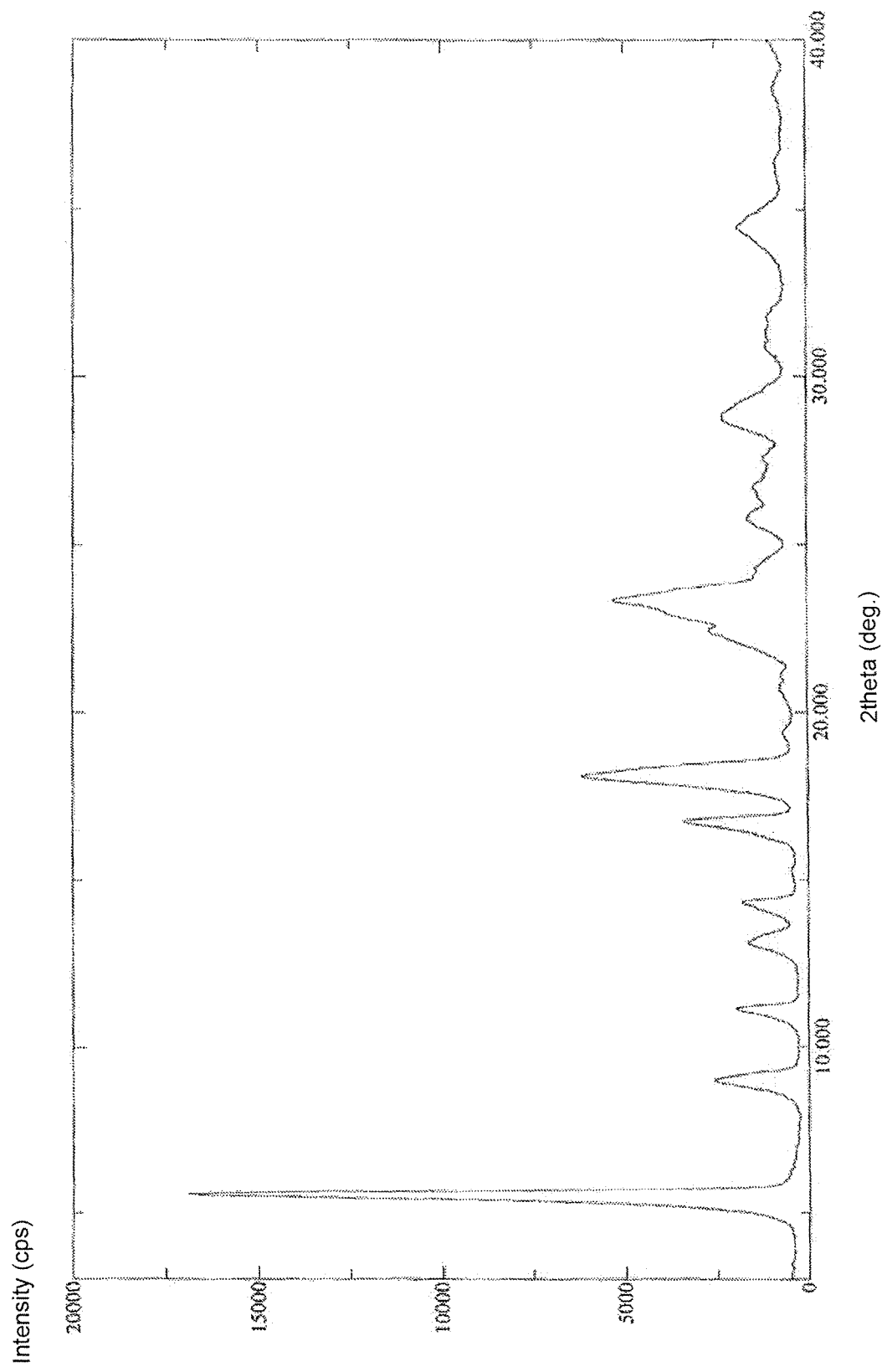
FIG. 5: A XRD of Regadenoson form A (prior art)

Polymorphic form A of compound 3 was prepared according to Experiment 4 of U.S. Pat. No. 8,106,183. The obtained sample was analyzed by XRD spectroscopy and corresponds to Regadenson monohydrate polymorphic form A (FIG. 5)

Stability Data Registered on Compound 3 in the Polymorphic Forms A, E, F and Amorphous Qualified polymorphic forms A, E, F and amorphous form of compound 3 obtained according to Examples 3-6 were stored at 80° C. in inert atmosphere and at 90% RH and 20-25° C. for 96 hours. Samples stored at 80° C. in inert atmosphere were analyzed at 72 and 96 hours for purity (HPLC) and solid state (XRD); also the samples stored at 90% RH and 20-25° C. were analyzed after 96 hours for purity (HPLC) and solid state (XRD).

The stability data obtained on the variation of chromatographic purity (HPLC data) are shown in tables 1 and 2; the stability of the solid state of crystalline forms E, F and of the amorphous forms were checked by XRD on the samples stored for 96 hours at 80° C. under inert atmosphere (FIGS. 8-11).

TABLE 1

HPLC stability data of different polymorphic form of Regadenoson at 80° C. in inert atmosphere

| Time (hours) | Form A | Form E | Form F | Halo Amorphous | Form G |
|---|---|---|---|---|---|
| 0 | 99.5 | 99.6 | 99.8 | 99.7 | 99.8 |
| 72 | 99.5 | 99.4 | 99.7 | 99.7 | 99.8 |
| 96 | 99.5 | 99.6 | 99.7 | 99.7 | 99.8 |

TABLE 2

HPLC stability data of different polymorphic form of Regadenoson stored at 90% RH and 20-25° C.

| Time (hours) | Form A | Form E | Form F | Halo Amorphous | Form G |
|---|---|---|---|---|---|
| 0 | 99.5 | 99.6 | 99.8 | 99.7 | 99.8 |
| 96 | 99.5 | 99.7 | 99.8 | 99.7 | 99.8 |

We claim:

1. A process for the preparation of the amorphous form of Regadenoson of formula

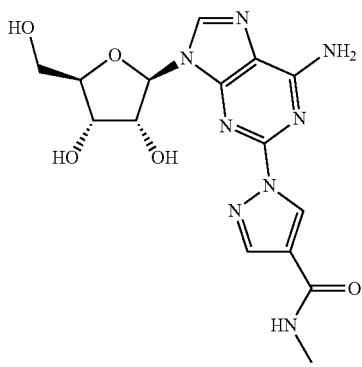 [SMILES: CNC(=O)c1cnn(-c2nc(N)c3ncn([C@@H]4O[C@H](CO)[C@@H](O)[C@H]4O)c3n2)c1]

according to the following scheme:

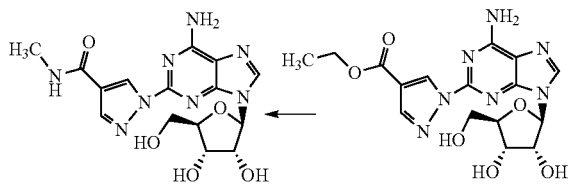 [SMILES: CNC(=O)c1cnn(-c2nc(N)c3ncn([C@@H]4O[C@H](CO)[C@@H](O)[C@H]4O)c3n2)c1 ; CCOC(=O)c1cnn(-c2nc(N)c3ncn([C@@H]4O[C@H](CO)[C@@H](O)[C@H]4O)c3n2)c1]

comprising the following steps:
a) reacting 2-(4-ethoxycarbonylpyrazol-1-yl)adenosine with a dry solution of methylamine in a linear $C_1$-$C_4$ alcohol or branched $C_3$-$C_4$ alcohol to provide a reaction mixture;
b) maintaining said reaction mixture under stirring at a temperature comprised between 60-100° C. in a pressure reactor in order to obtain the conversion of said 2-(4-ethoxycarbonylpyrazol-1-yl)adenosine into (1-{9-[(4S,2R,3R,5R)-3,4-dihydroxy-5-(hydroxymethyl)oxolan-2-yl]-6-aminopu-rin-2yl}pyrazol-4-yl)-N-methylcarboxamide;
c) removing unreacted methylamine from said reaction mixture;
d) cooling said reaction mixture from step c) to 10-25° C. at a cooling rate of 1-2° C. min;
e) diluting said reaction mixture from step d) 1:1 with a dry $C_1$-$C_4$ alcohol to provide a precipitate of amorphous (1-{9-[(4S,2R,3R,5R)-3,4-dihydroxy-5-(hydroxymethyl)oxolan-2-yl]-6-aminopurin-2yl}pyrazol-4-yl)-N-methylcarboxamide;
f) filtering said amorphous precipitate of step e) to isolate, and if desired
g) drying said precipitate.

2. The process according to claim 1, wherein in said step a) said $C_1$-$C_4$ alcohol is ethanol.

3. The process according to claim 2, wherein said ethanol is dry.

4. The process according to claim 1, wherein in said step a) said methylamine is in a concentration of between 10 and 40%.

5. The process according to claim 1, wherein in said step a) said 2-(4-ethoxycarbonylpyrazol-1-yl)adenosine is in a molar concentration of between 0.5 and 0.1 M.

6. The process according to claim 1, wherein in said step b) the reaction temperature is comprised between 80-85° C., the pressure is about 3 bar, the reaction time is about 30 hours.

7. The process according to claim 2, wherein step c) is carried out by removing methylamine by distillation under vacuum at 40° C., step d) is carried out by cooling the reaction mixture at 20-25° C., step e) is carried out by diluting the reaction mixture 1:1 with anhydrous ethanol and maintaining the reaction mixture under stirring for 30-60' at 20-25° C.

8. A Regadenoson solvate with one molecule of trifluoroethanol (Form E) comprising the following diagnostic peaks of X-ray diffraction spectrum in 2-theta (θ) values: 4.98, 12.08, 14.66, 17.60, 17.96, 19.20, 19.62, 20.24, 20.78, 21.08, 21.52, 23.18, 24.10 24.24, 25.08, 25.52, 26.02, 26.64, 27.36, 27.66, 27.84, and 28.74.

9. A process for the preparation of the Regadenoson solvate of claim 8 comprising:
a. treating amorphous Regadenoson in dry trifluoroethanol, at a temperature comprised between 15-50° C. for 0.5-1.0 hour to provide a reaction mixture;
b. filtering said reaction mixture, recovering a filtrate;
c. concentrating said filtrate under vacuum, to provide a residue;
d. maintaining said residue under vacuum.

10. The process according to claim 9, wherein in step a) the relative ratio between amorphous Regadenoson and trifluoroethanol is 1% w/w and the solution is maintained under stirring at 20-25° C. for 0.5 hour, in step c) the temperature of evaporation is about 40° C. and in step d) this temperature is maintained for 48 hours.

11. A Regadenoson solvate with 0.5 molecule of ethanol (Form F) comprising the following diagnostic peaks of X-ray diffraction spectrum in 2-theta (θ) values: 6.42, 10.38, 12.20, 12.80, 13.80, 16.24, 16.84, 19.28, 19.96, 20.20, 20.70, 22.00, 22.58, 23.38, 23.80, 25.04, 25.60, 26.28, 27.18, and 28.48.

12. A process for the preparation of the Regadenoson solvate of claim 11 comprising:
a. mixing amorphous Regadenoson in anhydrous ethanol w/w under inert atmosphere, to provide a suspension;
b. maintaining said suspension at a temperature comprised between 15-40° C. for 8-15 hours, to obtain a precipitate;
c. recovering said precipitate; and if desired
d. drying said recovered precipitate.

13. The process according to claim 12, wherein, in step a) the relative ratio between said amorphous Regadenoson and ethanol is 5% w/w and in step b) said suspension is maintained under stirring at 20-25° C. for 8-10 hours and in step d) said drying conditions are 60° C. for 72 hours.

14. A crystalline anhydrous Regadenoson (form G)) comprising the following diagnostic peaks of X-ray diffraction spectrum in 2-theta (θ) values: 8.24, 14.90, 17.70, 18.16, 19.84, 21.92, 26.16, 27.68, 30.44.

15. A process for the preparation of crystalline anhydrous Regadenoson of claim 14 comprising:

a. treating amorphous Regadenoson in dry ethanol for 60-90 hours to convert said amorphous Regadenoson into the thermodynamically more stable form G, to provide a reaction mixture;
b. cooling said reaction mixture down to 20-25° C. to provide a precipitate;
c. isolating said precipitate;
d. drying said isolated precipitate under vacuum at 40-60° C. for 24-72 hours.

16. A process for the preparation of crystalline anhydrous Regadenoson of claim 14 comprising:
a. mixing 2-(4-ethoxycarbonylpyrazol-1-yl)adenosine with a dry solution of methylamine in a linear $C_1$-$C_4$ alcohol or branched $C_3$-$C_4$ alcohol to provide a reaction mixture;
b. maintaining said reaction mixture under stirring at a temperature comprised between 60-100° C. in a pressure reactor in order to obtain the conversion of compound 2 into (1-{9-[(4S, 2R,3R,5R)-3,4-dihydroxy-5-(hydroxymethyl)oxolan-2-yl]-6-aminopurin-2yl}pyrazol-4-yl)-N-methylcarboxamide;
c. continuing the reaction for a time sufficient to convert Regadenoson into the more thermodynamically stable form G;
d. removing unreacted methylamine from said reaction mixture;
e. cooling said reaction mixture from step d) to 10-25° C. at a cooling rate of 1-2° C. min;
f. diluting said reaction mixture from step e) 1:1 with a dry $C_1$-$C_4$ alcohol to provide a precipitate of crystalline anhydrous Regadenoson;
g. isolating said precipitate of step f); and if desired
h. drying said precipitate.

17. A pharmaceutical composition, comprising the Regadenoson solvate of claim 8.

18. A pharmaceutical composition, comprising the Regadenoson solvate of claim 11.

19. A pharmaceutical composition, comprising the crystalline anhydrous Regadenoson of claim 14.

20. The process according to claim 9, wherein steps c) and d) are carried out at the same temperature.

21. The process according to claim 15, wherein in step a) dry ethanol is at a concentration of 4-7% w/v and step a) is carried out at a temperature between 70-78° C.

22. The process according to claim 15, wherein step c) is carried out by filtration.

23. A pharmaceutical composition, comprising a mixture of the Regadenoson solvate of claim 8, the Regadenoson solvate of claim 11 and/or the crystalline anhydrous Regadenoson of claim 14.

* * * * *